United States Patent [19]

Tachita et al.

[11] Patent Number: 4,552,152
[45] Date of Patent: Nov. 12, 1985

[54] ULTRASONIC DIAGNOSTIC APPARATUS USING DOPPLER EFFECT

[75] Inventors: Ryobun Tachita; Tsutomu Yano, both of Kawasaki; Hiroshi Fukukita, Tokyo; Kuniaki Fukaya, Atsugi; Akira Fukumoto, Machida, all of Japan

[73] Assignee: Matsushita Electric Industrial Company, Ltd., Kadoma, Japan

[21] Appl. No.: 513,323

[22] Filed: Jul. 13, 1983

[30] Foreign Application Priority Data

Jul. 14, 1982 [JP] Japan .................................. 57-122553

[51] Int. Cl.⁴ .............................................. A61B 10/00
[52] U.S. Cl. .................................................... 128/663
[58] Field of Search ...................... 128/663; 73/861.25

[56] References Cited

U.S. PATENT DOCUMENTS

4,265,126 5/1981 Papadofrangakis et al. ... 128/663 X

*Primary Examiner*—Kyle L. Howell
*Assistant Examiner*—Francis J. Jaworski
*Attorney, Agent, or Firm*—Cushman, Darby & Cushman

[57] ABSTRACT

Ultrasonic echo signals are detected in phase and integrated with a period corresponding to an ultrasonic pulse. The integrated values are sampled and the difference between two integrated values is successively frequency-analyzed.

9 Claims, 20 Drawing Figures

ULTRASONIC DIAGNOSTIC APPARATUS USING DOPPLER EFFECT

BACKGROUND OF THE INVENTION

The present invention relates to an ultrasonic diagnostic apparatus for use in measuring the speed of blood flow in a human body.

In the conventional ultrasonic Doppler method, ultrasonic pulses are emitted in a human body and a receiver extracts. Doppler signals of a desired number from ultrasonic echo signals returned from monitored portions of different depths in a blood vessel. The portions from which the Doppler signals are extracted are chosen between walls of the blood vessel of the human body. By analyzing the frequency of the Doppler signals from various portions in the blood vessel, a distribution of blood flow speed in the blood vessel is obtained. Because of a number of monitored points having different depths, the conventional ultrasonic diagnostic apparatus requires the same number of gate circuits, integration circuits, and sample holding circuits for extracting necessary Doppler signals. Moreover, the same number of gate signal generators are required. Therefore, large scale systems are required for monitoring at many different depths in a blood vessel of a human body.

SUMMARY OF THE INVENTION

According to the invention, a simply constructed ultrasonic diagnostic apparatus is obtained which allows simultaneous monitoring of a large number of pieces of blood flow information from different depths of the human blood vessel.

The ultrasonic diagnostic apparatus of the invention comprises an ultrasonic diagnostic probe for transmitting and receiving ultrasonic pulse signals, a detector for detecting phases of echo signals, means for integrating the detected signals, means for extracting plural integrated values and an analyzer for analyzing the frequency of a difference of two integrated values. The invention further provides an ultrasonic diagnostic apparatus which is able to monitor a vessel even during breathing of a human body.

BRIEF DESCRIPTION OF THE DRAWINGS

The invention will be further described with reference to the accompanying drawings, in which.

DETAILED DESCRIPTION

Figure 1:
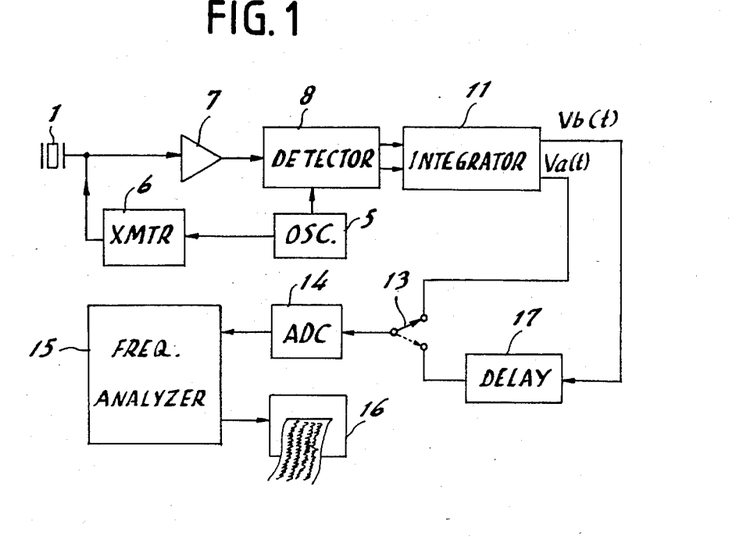
FIG. 1 is a block diagram of the ultrasonic diagnostic apparatus of the invention.

Referring now to FIG. 1, a clock oscillator 5 generates a reference pulse train of a frequency of 3 MHz which causes a transmitter 6 to generate a transmitting pulse train of a frequency of 4 Hz. An ultrasonic diagnostic probe 1 having transducers is excited by the transmitting pulse train to transmit a series of pulse signals to a human body. Each pulse signal is returned as an echo signal from a blood vessel of the human body and received by the ultrasonic diagnostic probe 1. During this time, the echo signal is in Doppler modulation under the influence of blood flow. The echo signal is amplified by amplifier 7 and supplied to a rectangular type detector 8. In the detector 8, the echo signal is multiplied by signals each of which is made from the 3 MHz reference pulse train by shifting 0° and 90° in phase. Each of the multiplied signals is integrated by an integrating circuit 11 to obtain $V_a(t)$ and $V_b(t)$ respectively. At this point, t illustrates a delayed time from an integration starting time of the integrating circuit. $V_a(t)$ signal is supplied to an analog to digital conversion 14 via a switch 13, while $V_b(t)$ signal is supplied to the analog to digital converter 14 via a delay line 17, thereby each being converted into digital signals.

Figure 2:
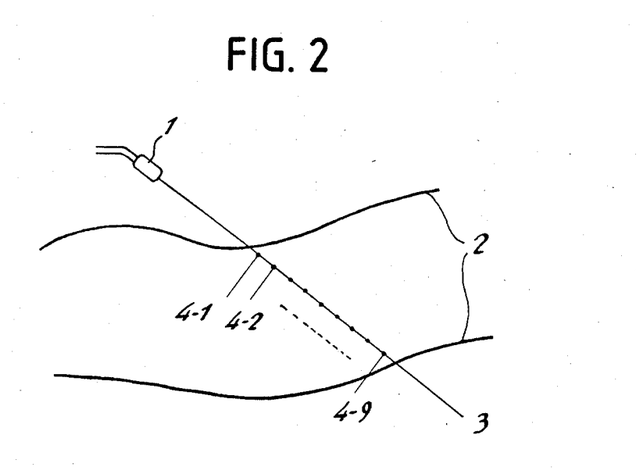
FIG. 2 is a cross-sectional view of a blood vessel for explaining the invention.

As illustrated in FIG. 2, if the number N of the points to be monitored 4-1, 4-2, . . . 4-9 by ultrasonic pulse beam 3 in the blood vessel 2 is nine (9), the analog to digital converter 14 repeats 10 times conversion for each of $V_a(t)$ and $V_b(t)$ and output signals $Va(t_n)$ and $Vb(t_n)$, where n is a value ranging from 0 to 9. The analog to digital conversion will be exactly described later.

In a frequency analyzer 15, Doppler signals $(V_a1, V_b1)$, $(V_a2, V_b2)$ . . . $(V_a9, V_b9)$ for nine (9) monitored points are calculated, from the output signals $Va(t_n)$ and $Vb(t_n)$ from the analog to digital converter 14, and frequency-analyzed, respectively. The output signals from the frequency analyzer 15 are supplied to a recoder 16 and recorded as blood flow information for the monitored points in the blood vessel.

Figure 3:
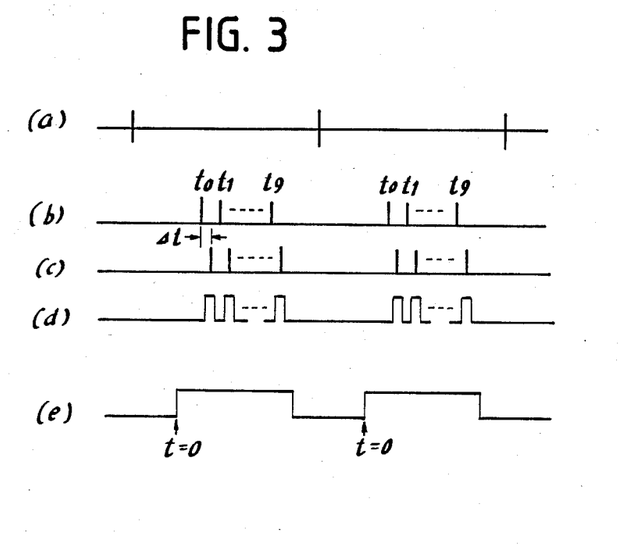
FIG. 3 is a timing chart showing analog to digital conversion timing of FIG. 1.

Referring now to FIG. 3, a wave form a shows a timing for transmitting or receiving ultrasonic pulse signals. A wave form b shows a timing for analog to digital conversion which is delayed $t_0$ to $t_9$ after the starting time of the integration. Assuming that the distances between each of the points to be monitored 4-1 to 4-9 in FIG. 1 are equal with each other, the ultrasonic pulse beam goes and comes back in a time $\Delta T$ along said distance, and times for receiving returned pulse beam from each of the point 4-1 to 4-9 are $T_1$ to $T_9$, the following formula is obtained.

$$\Delta T = T_{n+1} - T_n \tag{1}$$

$$T_n = \frac{t_{n-1} + t_n}{2} \tag{2}$$

$$\Delta T = t_n - t_{n-1} \tag{3}$$

$$V_a(t_n) = \int_0^{t_n} V_a(t)dt \qquad (4)$$

where, $V_a(t)$ is one of the output signals of the detector 8. The digital signal $V_a(t_n)$ expressed by the formula (4) is supplied to the frequency analyzer 15 via switch 13 and Doppler signals $V_{an}$ are calculated by the formula (5):

$$V_{an} = V_a(t_n) - V_a(t_{n-1}) \qquad (5)$$

where n is a value ranging from 1 to 9.

In the meantime, another output signal $V_b(t)$ of the integrating circuit 11 is delayed $\Delta t$ by the delay line 17 and converted into digital signal by the analog to digital converter 14. The timing in this case is shown c of FIG. 3, which is delayed $\Delta t$ in comparison with b of FIG. 3. As a result, $V_b(t_n)$ is expressed by the formula (6):

$$V_b(t_n) = \int_{\Delta t}^{t_n + \Delta t} V_b(t - \Delta t)dt \qquad (6)$$

where $V_b(t)$ is another output signal of the detector 8. The switch 13 changes the input signal for analog to digital converter 14 in $V_a(t)$ and $V_b(t)$ alternately with the timing of d of FIG. 3. In the frequency analyzer 15, Doppler signals $$V_{bn} = V_b(t_n) - V_b(t_{n-1}) \qquad (7)$$

where n is a value ranging from 1 to 9. The wave form e of FIG. 3 is a signal which determines the integral period of the integrating circuit.

By the above mentioned embodiment of the invention, it is possible to monitor blood flow information from many points having different depths in the blood vessel with simple circuit construction.

Figure 4:
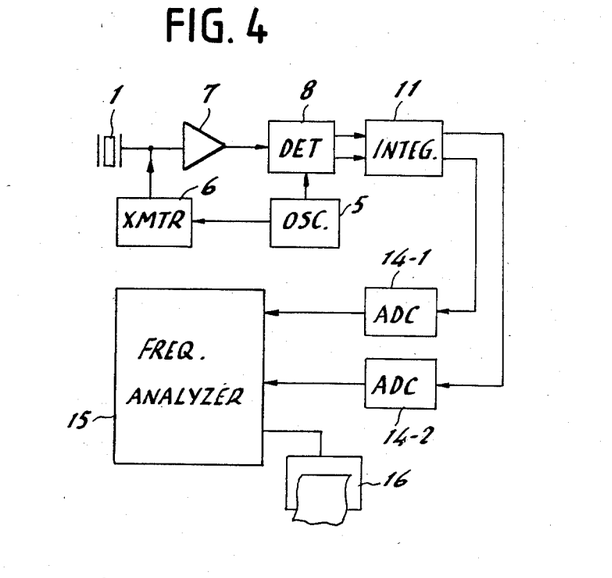
FIG. 4 is a block diagram of a modified embodiment of the invention.
Figure 5:
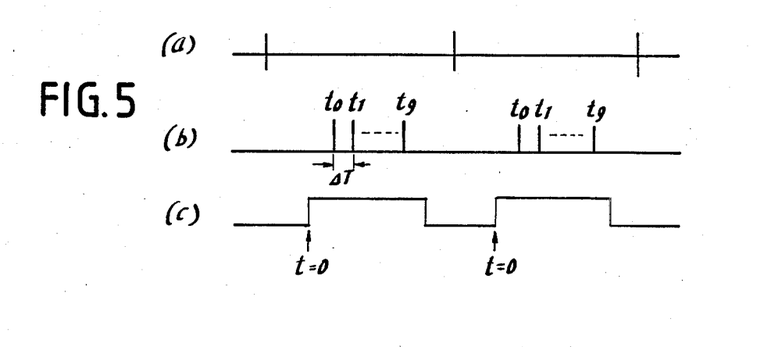
FIGS. 5 to 7 are timing charts each showing analog to digital conversion timing of FIG. 4.

Referring now to FIG. 4, another embodiment of the invention will be explained. Those corresponding to elements of FIG. 1 are marked by the same numerals as in FIG. 1. In the embodiment, the switch 13 and the delay line 17 in FIG. 1 is deleted and the analog to digital converter 14 in FIG. 1 is divided into two, each marked as 14-1 and 14-2. The analog to digital converter 14-1 serves for processing the signal $V_a(t_n)$ and analog to digital converter 14-2 for $V_b(t_n)$. The timing for analog to digital conversion is shown in FIG. 5. The wave forms a and b of FIG. 5 correspond to those of a and b of FIG. 3 and the wave form c of FIG. 5 corresponds to that of e of FIG. 3. Analog of digital conversions are performed in parallel by analog to digital converters 14-1 and 14-2 with the time interval $\Delta T$ from $t_0$ to $t_9$. The analog to digital conversion in each of the analog to digital converter 14-1 and 14-2 is repeated 10 times per one transmitting cycle. This embodiment is more simple than that of FIG. 1 because of no processing for switching or time delaying.

Figure 6:
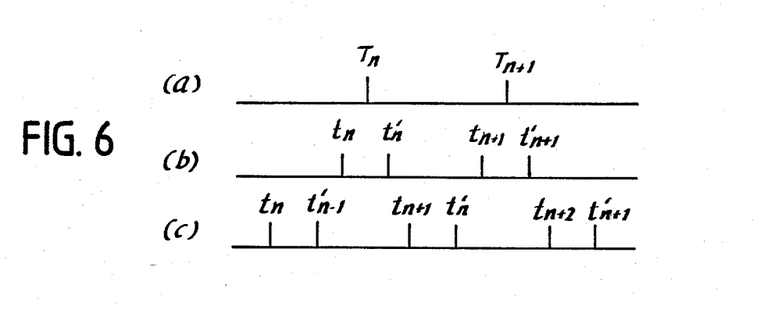

FIG. 6 shows another analog to digital conversion timing of the embodiment shown in FIG. 4. The timing $T_n$ and $T_{n+1}$ in FIG. 6a are the timing for extracting Doppler signals and the time intervals from $t_n$ to $t'_n$ and $t_{n+1}$ to $t'_{n+1}$ in FIG. 6b are the integration periods for the integrating circuit 11 in FIG. 4. During this time, analog to digital conversions are performed with the timing $t_n$, $t'_n$, $t_{n+1}$ by the analog to digital converters 14-1 and 14-2 in FIG. 4 to extract the Doppler signals $V_{an}$ and $V_{bn}$ by the formulae (8) and (9):

$$V_{an} = V_a(t'_n) - V_a(t_n) \qquad (8)$$

$$V_{bn} = V_b(t'_n) - V_b(t_n) \qquad (9)$$

In this case $t_n$ and $t'_n$ are expressed by the following formula (10):

$$T_n = \frac{t_b + t'_n}{2} \qquad (10)$$

Moreover, the integration periods b of FIG. 6 can be replaced by the periods from $t_n$ to $t'_{n-1}$, $t_{n+1}$ to $t'_n$ and $t_{n+2}$ to $t'_{n+1}$ as illustrated in FIG. 6c.

Figure 7:
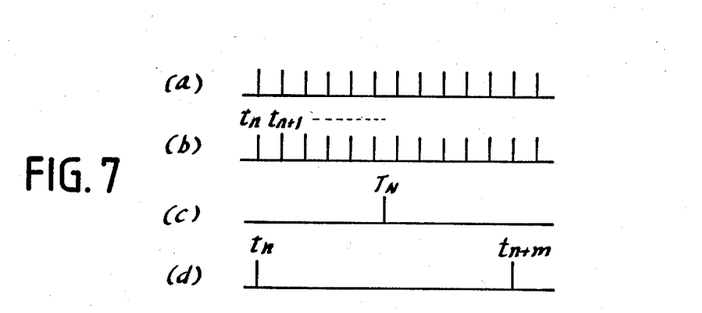

Referring now to FIG. 7, further analog to digital conversion timing of the embodiment of FIG. 4 will show the reference signal previously described and FIG. 7b shows the analog to digital conversion timing which is similar to the timing of the reference signal a. $T_N$ in FIG. 7c is the timing for extracting the Doppler signal and can be selected freely from the timing $t_n$ or the timing between $t_n$ and $t_{n+m}$ which corresponds to the integration period shown in FIG. 7d. The integration period is n times the analog to digital conversion interval. In this case, the Doppler signals $V_aN$, $V_bN$ and the timing for extracting the Doppler signal are determined by the following formulae (11) to (13):

$$V_aN = V_a(t_{n+m}) - V_a(t_n) \qquad (11)$$

$$V_bN = V_b(t_{n+m}) - V_b(t_n) \qquad (12)$$

$$T_N = \frac{t_n + t_{n+m}}{2} \qquad (13)$$

In this manner, the Doppler signals can be extracted by only selecting digital signals and subtracting operations of the same. As a result it is possible to determine freely the portion of the Doppler signals to be extracted and the integrating period therefor.

The blood vessel 2 in FIG. 2 is usually shifted by breath or motion of the human body. Therefore, the monitored point shall be shifted by following the shift of the blood vessel. The embodiments following the shift of the blood vessel will be explained hereinafter.

Figure 8:
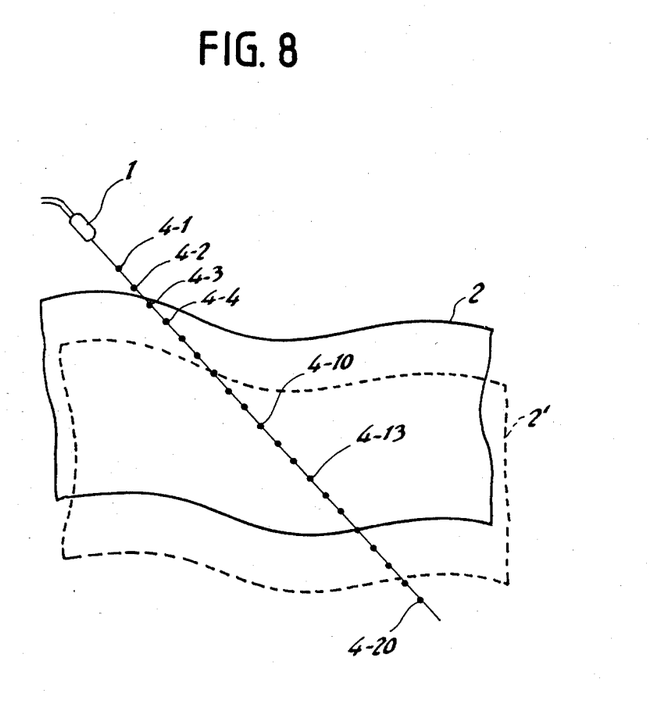
FIG. 8 is a cross-sectional view of the blood vessel in case of shifting the blood vessel toward an ultrasonic diagnostic probe.

Referring to FIG. 8, the relationship between the ultrasonic pulse beam and the blood vessel is shown. Assuming that the blood vessel shown by a solid line 2 is shifted to a different location indicated at a dotted line 2', twenty monitoring points 4-1, 4-2 . . . 4-20 are selected so as to cover an entire shifting range of the blood vessel.

Figure 9:
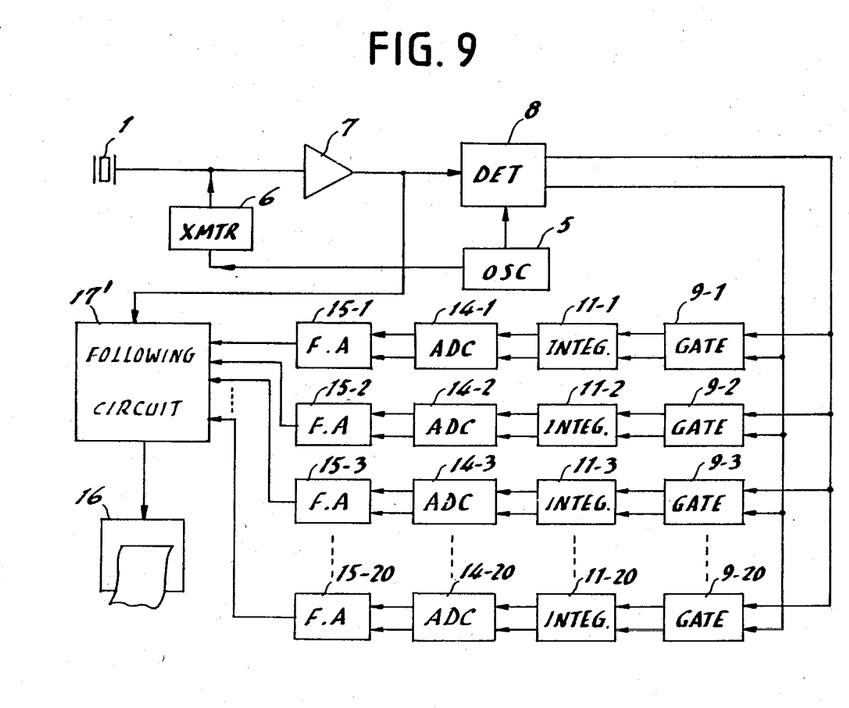
FIG. 9 is a block diagram of another modified embodiment of the invention.

FIG. 9 is a block diagram for the embodiment. Numerals 1, 5, 6, 7, 8 and 16 are the same portions as those of FIG. 1. Gate circuits 9-1 to 9-20 correspond to the monitored points 4-1 to 4-20 in FIG. 8, and each extracts the output signals $V_a$ and $V_b$ for corresponding periods. The outputs of the gate circuits 9-1 to 9-20 are integrated by integrating circuits 11-1 to 11-20, respectively, and output the Doppler signal $V_a$ and $V_b$, respectively. The signals $V_a$ and $V_b$ are converted into digital signals by analog to digital converter 14-1 to 14-20 and frequency analyzed by frequency analyzer 15-1 to 15-20 as is described in FIG. 1. Following circuit 17' selects one of the outputs from the frequency analyzer 15-1 to 15-20 and supplies a blood flow information to the recorder 16.

The following circuit 17' will be explained with reference to FIG. 10. The echo signal from the amplifier 7 is supplied to a blood vessel wall detecting circuit 17-1 which detects the position of the blood vessel wall. The detecting circuit 17-1 is constructed by a well known peak detecting circuit which detects peak portion of the echo signal. The detected output signal by the detecting circuit 17-1 is supplied to a selecting circuit 17-2 which controls a switching circuit 17-3 by the output signal of the detecting circuit 17-1, and one of the output signals from the frequency analyzers 15-1 to 15-20 is selected as the blood flow speed information. The selected blood flow speed information signal is supplied to subtracting circuit 17-5 and from which an average shift speed of the blood vessel in the ultrasonic beam direction is subtracted. The average shift speed of the blood vessel is obtained by the speed detecting circuit 17-4 which calculates the average shift speed of the blood vessel with the amount of shifts of the output signals of the detector 17-1 and the time required therefor. The output of the subtracting circuit 17-5 is supplied to the recorder 16. FIG. 11 shows the each signal which is supplied to the detecting circuit 17-1. Waveform a corresponds to the signal for blood vessel 2 in FIG. 8 and waveform b for blood vessel 2' in FIG. 8. The shift of the peak thereof gives the amount of the shift of the blood vessel.

Figure 10:
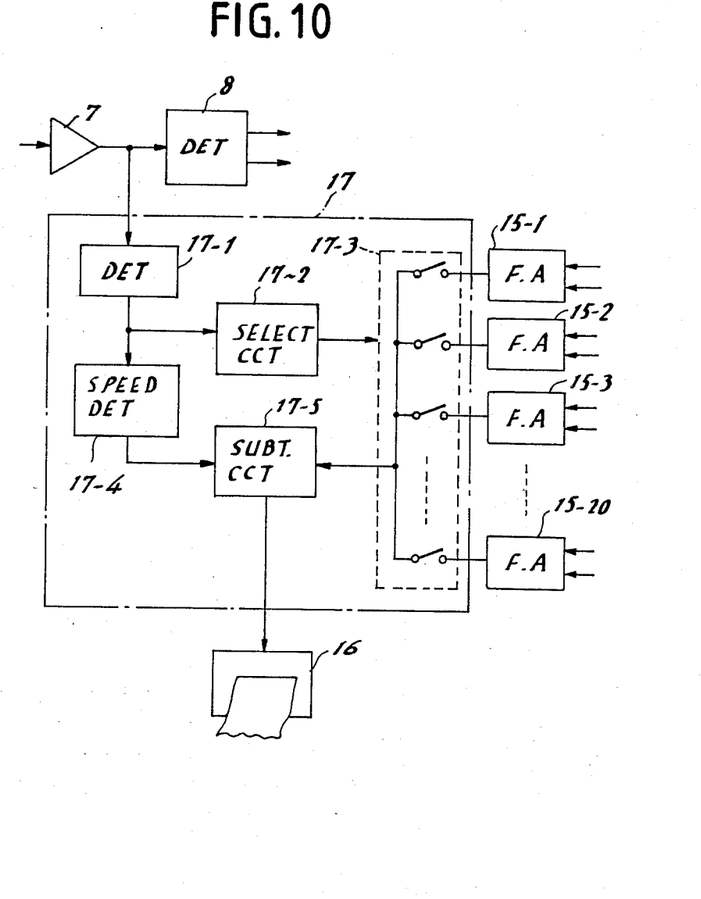
FIG. 10 is a block diagram of further modified embodiment of the invention.
Figure 11:
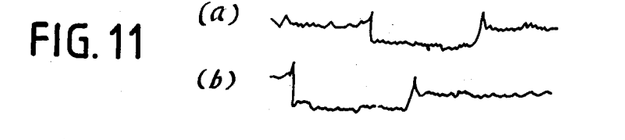
FIG. 11 is an example of an echo signal of the invention.
Figure 12A:
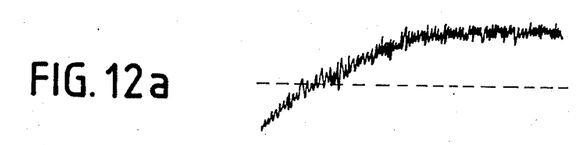
FIGS. 12(a)–12(c) are waveforms of the parts of the block diagram of FIG. 10.
Figure 12B:
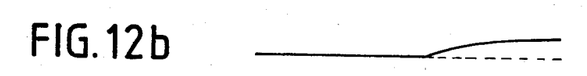
Figure 12C:
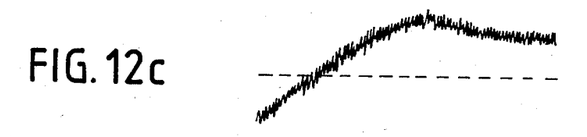

FIG. 12 shows wave forms of the parts of the block diagram in FIG.10. a shows the blood flow speed information selected by the switching circuit 17-3, b shows the shifting speed information of the blood vessel detected by the speed detecting circuit 17-4, and c shows the blood flow speed information output from the subtracting circuit 17-5 which corresponds to the difference between the waveforms a and b. The shifting speed V of the blood vessel illustrated in FIG. 7b is calculated by the formula (14):

$$V = V \cdot \frac{\tan \alpha}{\tan \alpha - \tan \beta} \quad (14)$$

where V is an assumed speed detected from the echo signal, $\alpha$ is an angle formed between the direction of the ultrasonic pulse beam and the blood vessel wall, and $\beta$ is an angle formed between the direction of the ultrasonic pulse wall and the shift direction of the blood vessel.

Figure 13:
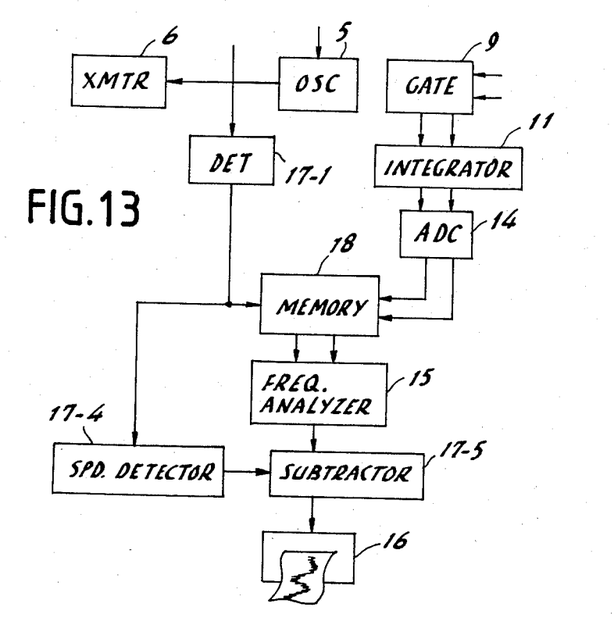
FIG. 13 is a block diagram of a further modified embodiment of the invention.
Figure 14A:
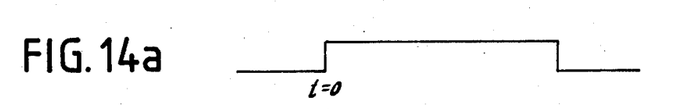
FIGS. 14(a)–14(b) are timing charts of analog to digital conversion in FIG. 13.
Figure 14B:
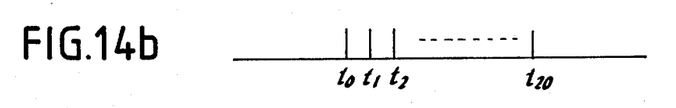

Referring now to FIG. 13, a further embodiment of the invention is illustrated. The same parts as those of FIG. 1, FIG. 9 and FIG. 10 are marked by the same numerals. Reference numeral 18 is a memory. The outputs $V_a$ and $V_b$ from the detector 8 are extracted by the gate circuit 9 with a gate signal shown in FIG. 14a. The extracted signal involves all the signals corresponding to the points 4-1 to 4-20 in FIG. 8. The extracted signal is integrated by the integrating circuit 11 and converted into digital signals $V_a(t_n)$ and $V_b(t_n)$ by the analog to digital converter 14 at the timing $t_0$ to $t_{20}$ illustrated in FIG. 14b, where n is a value ranging from 0 to 20. In this case $V_a(t_n)$ and $V_b(t_n)$ are represented by the formulae (15) and (16):

$$V_a(t_n) = \int_0^{t_n} V_a(t)dt \quad (15)$$

$$V_b(t_n) = \int_0^{t_n} V_b(t)dt \quad (16)$$

In addition, the timing $T_n$ for extracting Doppler signal corresponding to the points 4-1 to 4-20 in FIG. 8 is represented by the formula (17):

$$T_n = \frac{t_{n-1} + t_n}{2} \quad (17)$$

where n is a value ranging from 1 to 20. The output signals $V_a(t_n)$ and $V_b(t_n)$ of the analog to digital converter 14 are supplied to the memory, wherein the Doppler signals $V_{an}$ and $V_{bn}$ are calculated by the formulae (18) and (19) and stored therein.

$$V_{an} = V_a(t_n) - V_a(t_{n-1}) \quad (18)$$

$$V_{bn} = V_b(t_n) - V_b(t_{n-1}) \quad (19)$$

The memory 18 takes in the latest $V_{an}$ and $V_{bn}$ one after another each time the ultrasonic pulse transmits or receives, and stones $V_{an}$ and $V_{ab}$ for 128 times of transmissions or receptions of the ultrasonic pulses. The blood vessel wall detecting circuit 17-1 detects the position of the blood vessel wall as mentioned in FIG. 10, whereby the n value corresponding to pertinent monitored point is determined. The memory 18 sends to the frequency analyzer 12 the $V_{an}$ and $V_{bn}$ signals of last 128 times of transmissions or receptions corresponding to said n value. The output of the frequency analyzer 15 is supplied to the subtracting circuit 17-5 wherein the blood vessel speed which is detected by the speed detecting circuit 17-4 is subtracted from the output of the frequency analyzer 15 as mentioned in FIG. 10. The output of the subtracting circuit 17-5 is recorded by the recorder 16. Because of the use of the memory 18, it is possible to decrease the number of complex frequency analyzers to one (1) by reading out only the data necessary for frequency analysis.

In the embodiments shown in FIGS. 10 and 13, it is possible to eliminate the speed detecting circuit 17-4 and subtracting circuit 17-5, especially when the shifting speed of the blood vessel is relatively slow in comparison with the speed of blood flow.

Figure 15:
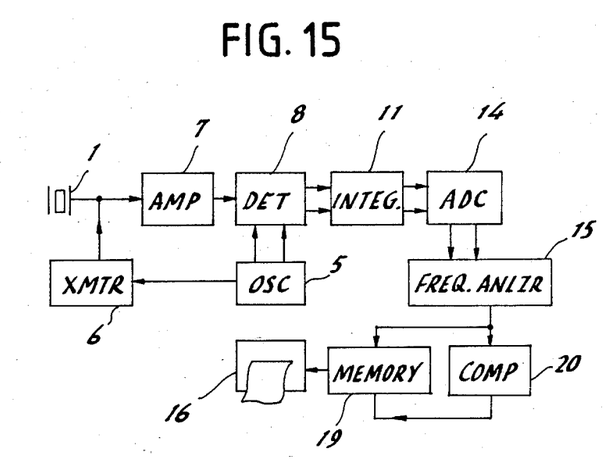
FIG. 15 is a block diagram of a further modified embodiment of the invention.

Referring now to FIG. 15, a further embodiment of the invention will be explained. The same parts as those of FIG. 1 or FIG. 13 are marked by the same numerals. As the same manner of FIG. 1, the outputs of the integrating circuit 11 are converted into digital signal by the analog to digital converter 14 and supplied to the frequency analyzer 15. The frequency analyzer 15 extracts the Doppler signal by operating the digital signals as in FIG. 1, whereby the blood flow speed distribution corresponding to each of the mentioned points is obtained. The thus obtained blood flow speed information is stored in the memory circuit 19 during the period of one pulsation of the subject heart. In the mean time, the blood flow speed information corresponding to each of the monitored points are compared with each other by a blood flow speed comparing circuit 20 to extract the point where maximum blood flow speed in observed. The point thus extracted is determined as the mid point of the blood vessel.

The blood flow speed information stored in the memory circuit 19 is selectively read out on the basis of said determined mid point and recorded by the recorder 16.

Figure 16A:
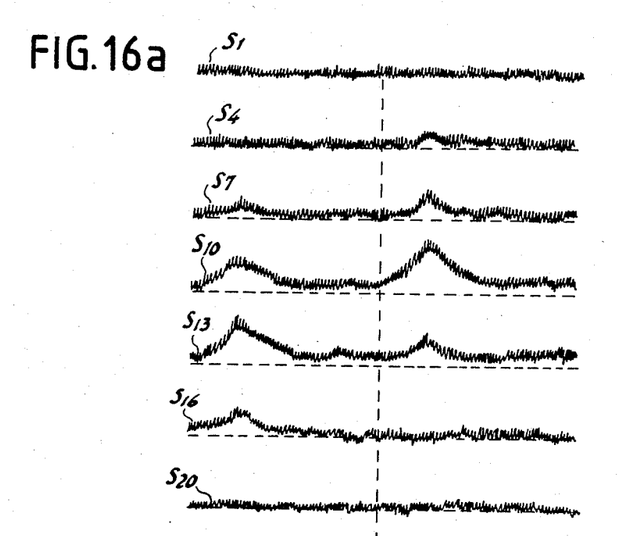
FIGS. 16(a)–16(b) are waveforms of the parts of the block diagram of FIG. 15.

Referring now to FIG. 16a, time variation of the blood flow speed distibution at the points 4-1, 4-4, 4-7, 4-10, 4-13, 4-16 and 4-20 in FIG. 8 is illustrated as the waveforms $S_1$, $S_4$, $S_7$, $S_{10}$, $S_{13}$, $S_{16}$ and $S_{20}$, respectively. The waveforms $S_1$ and $S_{20}$ show no blood flow because the points 4-1 and 4-20 are out of the blood vessel. The waveforms $S_{10}$ and $S_{13}$ show rapid pulsive streams of the blood and this teaches that the points 4-10 and 4-13 are the points near the center point of the blood vessel. In the time interval $t_1$ of one pulsation, the wave form $S_{13}$ shows the most rapid streams; therefore, the point 4-13 is determined as the center of the blood vessel. At this time, the wave form $S_{13}$ within the period $t_1$ is extracted from the memory circuit 19 as illustrated in FIG. 15b. In the next pulsation period $t_2$, the waveform $S_{10}$ shows the most rapid streams; therefore, the point 4-10 is determined as the center of the blood vessel, and the wave form $S_{10}$ within the pulsation period $t_2$ is outputted from the memory circuit 19.

Figure 16B:
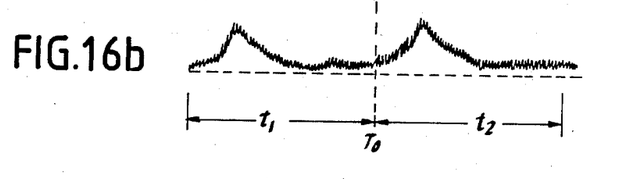

In the embodiment in FIG. 16b, the blood flow speed information at the center of the blood vessel is extracted. In addition to this, the blood flow speed information at other points of the blood vessel can be extracted on the basis of the center of the blood vessel. Moreover, it is possible to display the variation of the blood flow speed distribution in the blood vessel in time sequentially, by simultaneously outputting the blood flow speed information corresponding to plural positions in the blood vessel. This enables determination of flux or viscosity of the blood. Thus, the blood flow speed information at any position in the blood vessel is obtained by automatically following the shift of the blood vessel in a simple manner by determining the position of the blood vessel in comparing the blood flow speed obtained from plural positions in the blood vessel and selectively outputting the blood flow information.

What is claimed is:

1. An ultrasonic diagnostic apparatus comprising:
   an ultrasonic diagnostic probe means for transmitting and receiving ultrasonic pulse signals;
   detector means coupled to said ultrasonic diagnostic probe means for detecting phases of signals received by said ultrasonic diagnostic probe means and for producing output signals indicative of said phases;
   means coupled to said detector means for integrating said phase indicative signals during a timing period corresponding to one of transmitting and receiving timing of respective said ultrasonic pulse signals by said probe means and for producing integrated signals as output;
   means coupled to said integrating means for selecting a plurality of said integrated signals during a said period of integration; and
   means coupled to said selecting means for analyzing the frequency of the difference of at least one pair of said plurality of integrated signals selected by said selecting means.

2. An ultrasonic diagnostic apparatus as in claim 1, wherein said selecting means includes analog to digital converting means for converting said plural integrated signals into digital signals prior to operation of said frequency analysis means thereon.

3. An ultrasonic diagnostic apparatus as in claim 1, further comprising memory means for storing said integrated signals each time said ultrasonic probe transmits or receives.

4. An ultrasonic diagnostic apparatus as in claim 1, further comprising detecting means for relating the temporal occurrence of said integrated signals with various distances from said probe delineated as respective positions within a subject object and for outputting the same as related respective positions, and means responsive to said output of said detecting means for selecting one of output signals from said frequency analyzing means in accordance wtih said related respective positions.

5. An ultrasonic diagnostic apparatus as claimed in claim 4, wherein said means for selecting output signals of said frequency analyzing means functions on the basis that said respective positions are indicative of a predetermined property of said integrated signals.

6. An ultrasonic diagnostic apparatus as claimed in claim 5, wherein said predetermined property is blood flow speed and said means for selecting further includes further means for determining the maximum blood flow speed indicated by said integrated signals at any given instant of time.

7. An ultrasonic diagnostic apparatus as claimed in claim 6, wherein one of said respective positions for which said further means determines said maximum blood flow speed defines a desired position.

8. An ultrasonic diagnostic apparatus as claimed in claim 6, wherein one of said respective positions other than one for which said further means determines said maximum blood flow speed defines a desired position.

9. An ultrasonic diagnostic apparatus as claimed in claim 5, wherein said selecting means selects an output signal of said frequency analyzing means by comparing said related respective positions output by said detecting means occurring within one pulsation period.

* * * * *